United States Patent [19]

Lepper, Jr.

[11] 4,113,386

[45] Sep. 12, 1978

[54] PHOTOMETER

[75] Inventor: James M. Lepper, Jr., Redlands, Calif.

[73] Assignee: Climet Instruments Company, Redlands, Calif.

[21] Appl. No.: 725,027

[22] Filed: Sep. 20, 1976

[51] Int. Cl.² .................... G01N 21/00; G01N 21/26
[52] U.S. Cl. ................................. 356/103; 250/574
[58] Field of Search ............... 356/103, 104, 207, 208, 356/209; 250/574

[56] References Cited

U.S. PATENT DOCUMENTS

| | | | |
|---|---|---|---|
| 2,812,686 | 11/1957 | Sinclair | 356/103 |
| 3,231,748 | 1/1966 | Haessler | 356/103 |
| 3,361,030 | 1/1968 | Goldberg | 356/103 |
| 3,787,122 | 1/1974 | Lepper | 356/207 |

*Primary Examiner*—Samuel W. Engle
*Assistant Examiner*—Donald P. Walsh
*Attorney, Agent, or Firm*—Michael, Best & Friedrich

[57] ABSTRACT

The forward light scattering photometer for analyzing particles dispersed in a fluid includes a cylindrical housing enclosing a pair of axially spaced, spherical-surfaced, bi-convex lenses which provide axial focusing of the lamp image in an intermediate light scattering chamber through which the sample being analyzed is flowed. Such lenses provide axial focusing with no circumferential aberations and only radial aberations. Light traps having radial borders, such as semicircular blank off discs, are located on the upstream or lamp side of each lens to provide an image having sharp radial edges, thereby eliminating the need for high quality lenses adapted to correct for spherical aberations.

The lenses are shielded from contamination by particles from the sample by a stream of purge air introduced into the housing at a location near each lens and tangentially with the housing bore so as to create a stable vortexing flow of the purge air in the vicinity of each lens.

11 Claims, 4 Drawing Figures

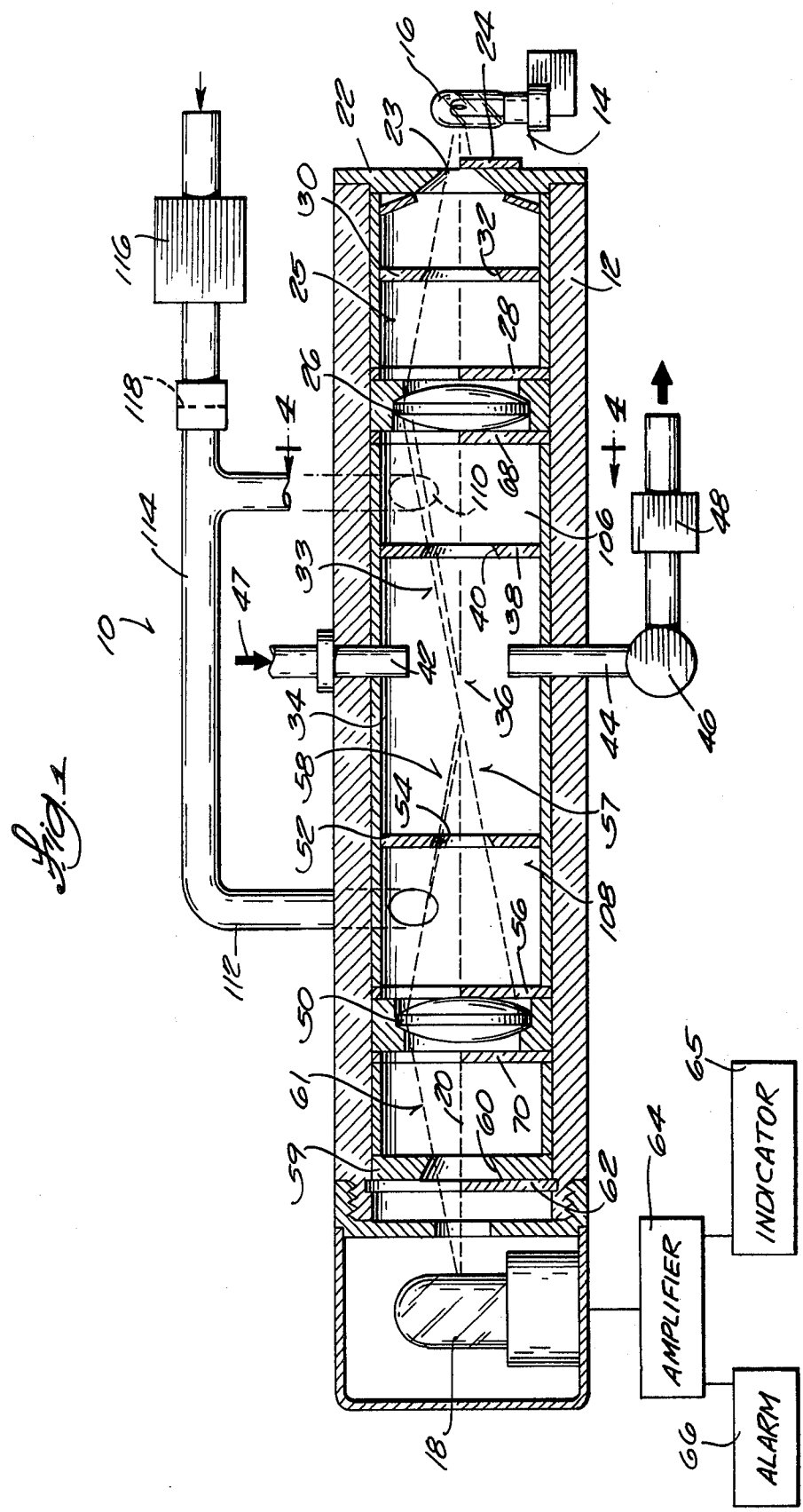

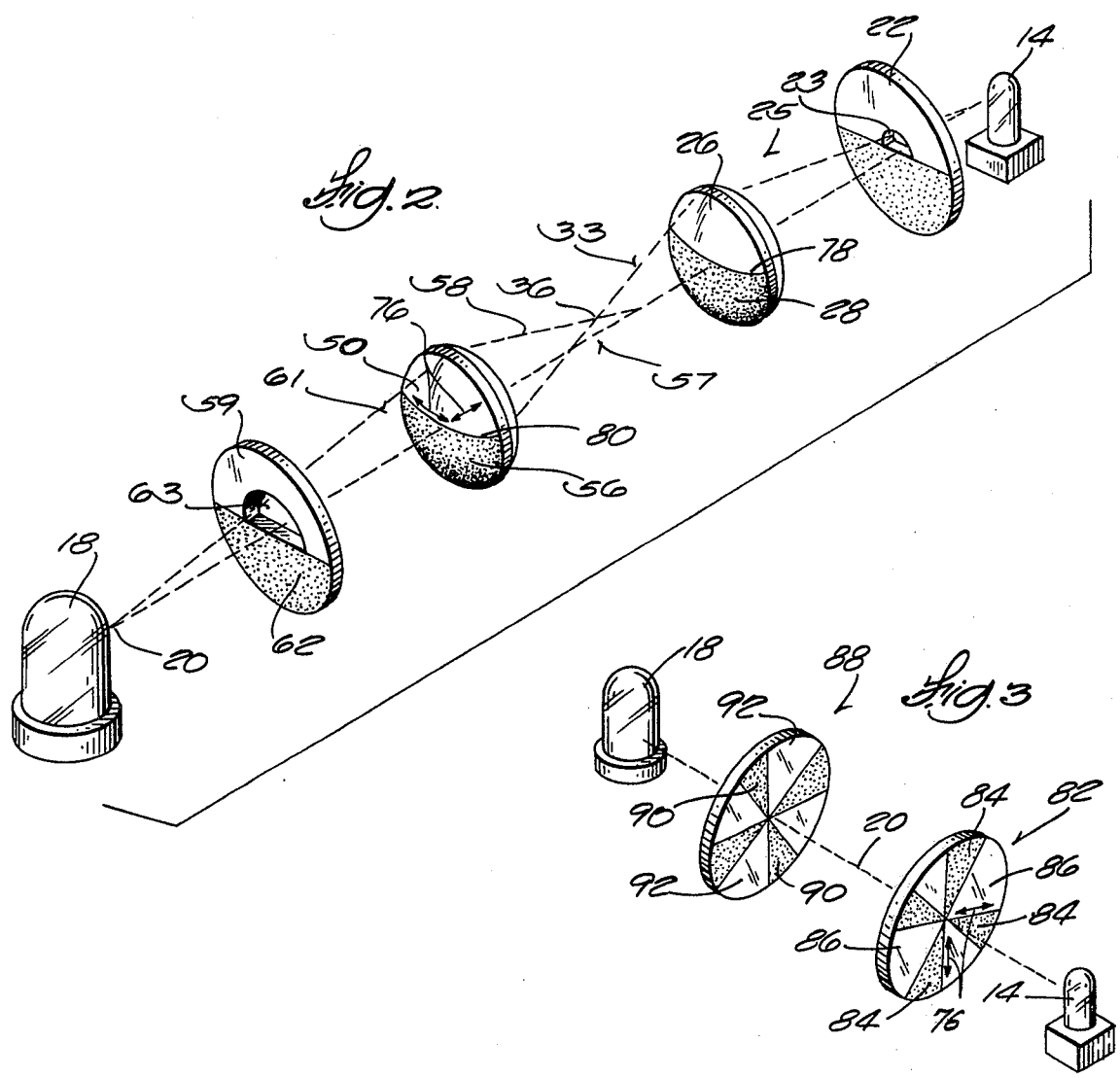
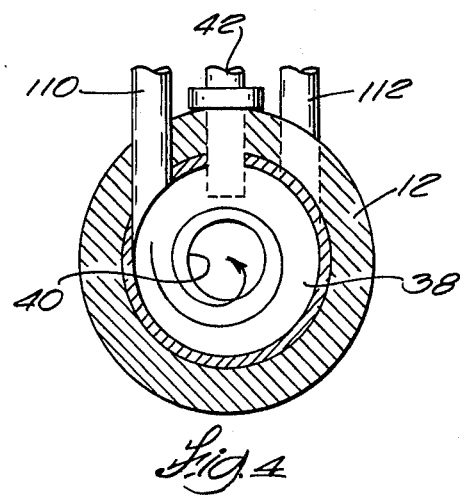

PHOTOMETER

BACKGROUND OF THE INVENTION

This invention relates to devices for measuring particles suspended in a fluid and, more particularly, to forward light scattering photometers.

One type of device used for measuring the size and/or concentration of paticles suspended in a transparent fluid is photometer employing forward light scattering, i.e., a beam of light is projected through a flow stream of the fluid and the amount of light scattered out of the beam by the particles is measured by a light sensing or detecting means. Such photometers are used to monitor atmospheric pollution by smog, dust, pollen, etc., to monitor the presence of airborne pollutants of contaminants in an area where a high degree of cleanliness is required, such as laboratories, hospitals and rooms where dirt-sensitive equipment is operating or is being assembled, and to count the number of particles suspended in a liquid, such as cells in a blood sample or particles in hydraulic fluids.

To be most effective, such a photometer should be arranged so that only the light scattered by the particles in the sample being analyzed reaches the light detector. Typical prior art arrangements include a first lens for focusing an illuminating beam in a sensing region through which the sample is flowed, a second lens for focusing the scattered light onto the light detector and a circular light trap which is located between the sensing region and the second lens and is arranged to interrupt the unscattered portion of the illuminating beam and permit only the scattered light to pass through the second lens to the light detector.

The light scattering caused by the sample particles takes place primarily at small angles to the original path of the illuminating beam. To obtain maximum collection of the scattered light by the light detector, the light trap should be exactly the same size as the illuminating beam so that light rays scattered by only a slight deviation will pass the light trap and fall onto the second lens. If there are any spherical aberations, the illuminating beam cannot be perfectly focused on the light trap, i.e., the outer edge of the beam is not distinct. Consequently, the light trap usually must be somewhat larger than the illuminating beam so that the unscattered portions spilling over into the scattered light path do not travel to the light detector. As the overlapping margin of the light trap is increased, additional amounts of the scattered light are intercepted with resultant inaccurate measurements.

In order to minimize the overlapping margin of the light trap, prior art devices usually employ high quality lenses which will provide a very sharp image of the illuminating beam on the light trap and thereby minimize spillover of incident beams into the path of the scattered light. Such a lens typically employ doublets to correct for spherical aberations and are quite expensive.

When photometers are used for analyzing an aerosol sample, some means should be provided for shielding the lenses from the sample so that the particles from the sample will not deposit on the lenses. Any particles deposited on the lenses would produce inaccurate measurement by the light detector because they will cause a spurious scattering of the light.

SUMMARY OF THE INVENTION

A principal object of the invention is to provide a forward light scattering photometer which is arranged to permit the use of inexpensive lenses.

Another principal object of the invention is to provide a forward light scattering photometer which can be used to analyze aerosol samples and includes simplified means for preventing the sample from contacting the lenses used for focusing the illuminating beam.

Other objects, aspects and advantages of the invention will become apparent to those skilled in the art upon reviewing the following detailed description, the drawings and the appended claims.

The forward light scattering photometer provided by the invention includes an elongate housing, a light source for providing a beam of light along an axial path through the housing, a light detecting means, and a pair of simple, spherical-surfaced, bi-convex lenses disposed in axially spaced relationship inside the housing for focusing the light beam in a sensing or light scattering chamber through which a particle-containing sample is flowed and for focusing light scattered by the sample particles onto the light detecting means. The lenses are an inexpensive type which provide axial focusing of the lamp image with radial aberations and substantially no circumferential aberations. The effect of the radial aberations are compensated for by using light traps which have radial borders so that an image having sharp radial edges is formed even though it is out of focus in other dimensions.

In accordance with a preferred embodiment, a first semicircular light trap is located adjacent the upstream side of and masks at least one half of a first lens which focuses the lamp image in the scattering chamber and a second semicircular light trap is located adjacent the upstream side of and masks at least one half of a second lens which focuses the scattered light onto the light detecting means. With this arrangement, a generally converging semiconical beam of light is focused in the focal region of the scattering chamber. The portion of the focused beam unscattered by the sample particles diverges from the focal region as one half a cone and is absorbed by the second light trap. Light scattered by the sample particles diverges from the focal region as the other half of a cone and passes through the second lens to the light detecting means.

Also in accordance with the invention, means is provided for introducing a flow of purge air into the housing in a manner so that, when an aerosol sample is being analyzed, the lenses are shielded from contamination by the sample. More specifically, a pair of axially-spaced, centrally-apertured, light-absorbing discs are provided for separating the lens from the focal region. These discs define the scattering chamber and cooperate with the respective lens to define a purge chamber associated with each lens. The purge air is introduced into the purge chambers through an inlet which is arranged tangentially to the housing bore. With this arrangement, the purge air flows through the purge chambers and exits therefrom into the scattering chamber in a spiralling or vortexing pattern which minimizes flow of the aerosol sample from the scattering chamber into the purge chambers.

BRIEF DESCRIPTION OF THE DRAWINGS

FIG. 1 is a simplified sectional and partially diagrammatic view of a photometer embodying the invention.

FIG. 2 is a perspective diagrammatic representation of a portion of the structure of FIG. 1 illustrating the optics.

FIG. 3 is a perspective, diagrammatic representation of an alternate arrangement for the light traps.

FIG. 4 is a sectional view taken along the line 4—4 in FIG. 1.

DESCRIPTION OF THE PREFERRED EMBODIMENTS

A photometer embodying the invention will be described for use for analyzing airborne particles in an aerosol stream. It should be understood that the photometer can be adapted for other similar uses, including detection of particles suspended or colloidally dispersed in a substantially transparent liquid.

Referring to FIG. 1, the photometer 10 includes an elongate, generally cylindrical housing 12 having a cylindrical bore, a light source, such as a lamp 14, having a small area filament 16 (e.g., a quartz lamp), suitably supported at one end of the housing 12 (right end as viewed in FIG. 1) and a suitable light detector 18, such as a photomultiplier tube, supported at the other end of the housing 12 (left end as viewed in FIG. 1). The lamp filament 16 and the light sensitive portion of the light detector 18 lie on a longitudinal axis 20 which is substantially the center line of the housing 12.

A light beam from the lamp 14 is admitted into the housing 12 through an end plate 22 having a central circular aperture. The lower half of the end plate aperture is masked by a light-absorbing blank off 24 to provide a generally semicircular opening 23 through which the light beam passes. A diverging or expanding semiconical light beam (designated by reference numeral 25) passes through the end plate opening 23 and falls onto the upper half of a first lens 26 which is a simple, spherical-surfaced, bi-convex type and is located in symmetrical relationship to and transversely of the axis 20. The lower half of the first lens 26 is masked by a semicircular blank off disc or light trap 28 which intercepts any light rays falling below a horizontal plane intersecting the axis 20.

Disposed between the first lens 26 and the end plate 22 is a first light-absorbing disc 30 having a circular central aperture 32 which is disposed symmetrically about the axis 20 and through which the semiconical light beam passes. The first disc 30 is arranged to absorb spurious light reflected from other components inside the housing 12. The aperture 32 defines the radial border of the semiconical light beam 25 falling onto the first lens 26 and is sized to minimize the amount of rays falling beyond the outer periphery of the first lens 26. For example, if the first disc 30 is located midway between the lamp filament 16 and the first lens 26, the radius of the aperture 32 is one-half the radius of the first lens 26.

The semiconical light beam (designated by reference numeral 33) passing through the upper half of the first lens 26 is focused in a light scattering chamber 24. The aerosol sample being analyzed is introduced into the scattering chamber 34 and passed through the focal region of the light beam as explained below.

Located approximately midway between the focal region of the focused light beam (designated generally by the reference numeral 36) and the first lens 26 is a second light-absorbing disc 38 having a central circular aperture 40 which is disposed symmetrically about the axis 20 and through which the semiconical light beam 33 from the second lens 26 passes to the scattering chamber 34. The second disc 38 serves the same general function as the first disc 30, i.e., aids in controlling the radial border of the light beam and absorbs spurious light reflected from other components inside the housing 12.

The aerosol sample being analyzed is introduced into the scattering chamber 34 through an inlet nozzle 42 extending into one side of the housing 12 substantially perpendicular to the axis 20. The sample is exhausted from the opposite side of the housing 12 through an outlet conduit 44 which is coaxial with the inlet nozzle 42. This can be accomplished by a suitable pump 46, such as a conventional motor driven impeller or rotor type pump, which is connected in communication with the outlet conduit 44 and operates to draw a stream of air from the atmosphere being analyzed (represented by arrow 47) through the focal region 36 of the light beam via the inlet nozzle 42 and the outlet conduit 44. The pump 46 discharges the sample stream to atmosphere. The discharge of the pump 46 can be filtered with a conventional filter 48 to prevent contamination or recontamination of the area being analyzed and to collect particles for later inspection.

A second lens 50, which is the same type as the first lens 26 and is located downstream of the light beam focal area 36, focuses the light forwardly scattered by particles in the aerosol sample onto the light detector 18. Located approximately midway between the focal region 36 and the second lens 50 is a third light-absorbing disc 52 having a central circular aperture 54 which is disposed symmetrically about the axis 20 and through which the light beam (both the portion scattered by the aerosol sample particles and the portion unscattered by the aerosol sample particles) passes from the light scattering chamber 34 towards the second lens 50. The third disc 52 cooperates with the second disc 38 to define the scattering chamber 34 and otherwise serves the same general function as the first and second discs, i.e., aids in controlling the radial border of the scattered and unscattered portions of the light beam and absorbs spurious light reflected from other components inside the housing 12.

The portion of the light beam unscattered or undeviated by particles in the sample diverges from the focal region 36 as a lower half cone. A semicircular blank off disc 56 or light trap located in front of the second lens 50 absorbs the semiconical beam of unscattered light (designated by reference numeral 57) and prevents it from reaching the lower half of the second lens 50.

Light scattered by particles in the aerosol sample is re-emitted in all directions. However, the majority of the scattered light is emitted at small angles relative to the original path of the light beam, travels from the focal region 36 in an expanding or diverging upper half cone (designated by reference numeral 58), and falls onto the upper half of the second lens 50.

The second lens 50 focuses this semiconical beam of scattered light 58 onto the light sensitive element of the light detector 18. Located approximately midway between the second lens 50 and the light sensitive element of the light detector 18 is a fourth light-absorbing disc 59 having a central circular aperture 60 which is symmetrically disposed about the axis and through which the converging semiconical beam of scattered light (designated by reference numeral 61) passes from the second lens 50 to the light detector 18. The fourth disc 59 serves the same general function as the first disc 30.

Since only a semiconical light beam passes through the second lens 50, the lower half of the aperture 60 is masked by a semicircular blank off disc or light trap 62 to provide a semicircular opening 63 through which the semiconical scattered light beam 61 is admitted to the light detector 18. The primary purpose of the blank off 62 is to absorb spurious light reflected from other components inside the housing.

An electrical signal produced by the light detector 18, in response to the amount of scattered light 61 falling thereon, is fed to an amplifier 64. The amplifier 64 is electrically connected to a suitable indicator 65 which is arranged to monitor the amount of particles in the sample being analyzed and/or connected to a suitable alarm system 66 which is arranged to provide a visual or audible alarm signal when the concentration of particles in the sample exceeds a predetermined level.

The entire interior of the housing 12, including all the light-absorbing discs, the light traps, the blank off discs, the inlet nozzle, the outlet conduit, and all the exposed edges thereof, is coated with a light-absorbing material, such as black anodized aluminum, black photographic paint, oxidized copper or the like, so as to minimize stray light.

To further minimize stray light, semicircular blank off discs or light traps 68 and 70 preferably are located on the downstream side or back of the first and second lenses 26 and 50, respectively, to mask the lower half thereof. The primary purpose of these blank off discs is to absorb any light reflected from the lamp side or upstream side of the discs 38 and 59.

A photometer arranged in this manner has a contrast of the main light beam to the scattered light beam within the range of about 10,000:1 to about 1,000,000:1.

Reference is made to FIG. 2 for more detailed description of the optics provided by the lights traps and the lenses. FIG. 2 is a schematic representation of a portion of the structure described in connection with FIG. 1, namely, the lamp 14, the first and second lenses 26 and 50, the light traps 28 and 56, the end plate 22, the light detector 18 and the light-absorbing disc 59 in front of the light detector 18. To simplify the illustration, the light absorbing discs are shown flat and the light traps shown are part of the lenses.

As mentioned above, the first and second lenses 26 and 50 are simple, spherical-surfaced, symmetrical, biconvex lenses. Lenses of this type provide axial focusing with no circumferential aberations and only radial aberations. That is, a point on the longitudinal axis 20 is imaged on the axis and none of the rays fall outside a vertical plane intersecting the axis 20, i.e., there are no skew rays. Spherical aberations and chromatic aberations still occur causing the rays to intersect the axis 20 at different distances from the first lens 26. The light rays passing through the central portion of the first lens 26 focus long while the light rays passing through the peripheral portion of the lens 26 focus short and the resulting image is spread at the focal region.

The radial aberations produced by the simple lenses employed are illustrated by arrows 76 in FIGS. 2 and 3. By using the light traps with radial borders in accordance with the invention, an image having sharp radial edge can be formed although it is out of focus in other dimensions. In the embodiment illustrated in FIGS. 1 and 2, this radial border is provided by the use of semicircular light traps 28 and 56. The semiconical light beam 25 passing through the semicircular opening 23 in the end plate 22 falls onto the upper half of the first lens 26. The upper edge 78 of the first light trap 28 produces an image of the lamp having a sharp radial edge in the focal region 36 along the axis 20. The undeviated or unscattered light 57 passes from the focal region 36 as a diverging semiconical beam and is absorbed on the light trap 56. The aberations of the unscattered light 57 focused on a light trap 56 are radial to the center line of the lens 50 and do not cross the top edge 80 of the light trap 56. The light scattered by the particles of the sample is deviated in all directions and only the portion passing from the focal region 36 in the upper half cone 58 reaches a light detector 18 through the second lens 50.

The edge between the unscattered light beam 57 and the scattered light beam 58 is not always sharply defined. Therefore, the upper edges 78 and 80 of the light traps 28 and 56 preferably are arranged to extend a small distance, e.g., about 0.04 inch (1 mm), above the center line of the respective lenses.

While other spacings can be used, it is preferred to space the first lens 26 from the lamp filament 16, the second lens 50 from the light sensitive element of the light detector 18, and the two lenses relative to each other so that the lamp filament and its image are $2\,f_o$ from the lenses, on either side. Such spacing minimizes the overall length of the photometer. For instance, this spacing between each can be 2 inches giving an overall optical length of 8 inches. The lenses 26 and 50 can have different diameters and focal lengths; however, in order to optimize the design to permit use of the lenses having the lowest $f$ number available, the lenses preferably are identical.

While the use of semicircular light traps have been described and are preferred because of their simplicity, it should be understood that other light trap arrangements can be provided so long as the effect of radial aberations is minimized and the two light traps are substantially complementary, i.e., all the incident light allowed to pass through the first lens is absorbed by the light trap associated with the second lens.

An acceptable alternate arrangement for the light traps is shown in FIG. 3. The light trap 82 for the first lens 26 has a plurality of radially extending, fan-like, light-absorbing sectors 84 and light-transmitting sectors 86. The light trap 88 for the second lens 50 has a corresponding number of light-absorbing sectors 90 and light-transmitting sectors 92 which are respectively circumferentially aligned with the light-transmitting sectors 86 and the light-absorbing sectors 84 of the first light trap 88 so that each sector of unscattered light passing from the focal region 36 toward the second lens 50 is absorbed by a light-absorbing sector 90 on the second light trap 90. The light-absorbing and light-transmitting sectors of the two light traps 82 and 88 are substantially complementary. For example, if the first light trap 82 is 70% masked (black) and 30% unmasked (clear), then the second light trap 88 is substantially 30% unmasked and 70% masked.

When the alternate light trap arrangement illustrated in FIG. 3 is used, the apertures in the end plate and the light-absorbing disc located in front or upstream of the light detector can be provided with a corresponding shape to minimize stray light. Also, when light traps are used on the back or downstream side of the first and second lenses 26 and 50, each has the same shape as and is coaxial with the light trap located upstream of the respective lens.

It can be appreciated that, in either of these illustrated embodiments, the edges of the light traps extend radially relative to the axis 20 and are not concentric therewith. Accordingly, the radial aberations produced by the lenses 26 and 50 generally are not at right angles to these radially extending edges or borders and, therefore, do not tend to cross the edges or borders of the light traps with a resultant sharp contrast between the scattered and unscattered light.

A flow of clean air is introduced into the housing 12 in a manner to minimize the possibility of particles from the aerosol sample depositing on the lenses. Referring again to FIG. 1, the first lens 26 and the disc 38 cooperate to define a purge chamber 106 and the second lens 50 and the disc 52 cooperate to define a purge chamber 108. Clean air is introduced into each purge chamber 106 and 108 through respective inlets 110 and 112 connected to a manifold 114. Atmospheric air enters the manifold 114 through a filter 116 which removes all particles large enough to cause light scattering.

As best shown in FIG. 4, the inlets 110 and 112 are located tangentially to the generally cylindrical bore of the housing 12 so that the filtered air drawn into the purge chambers 106 and 108 by the pump 46 flows through the purge chambers in a spiralling or vortexing pattern toward the aperture of the respective discs 38 and 52. The purge air flows through the respective disc apertures into the scattering chamber 34 and is eventually exhausted therefrom along with the aerosol sample through the outlet conduit 44.

Since the peripheral, circular flow must converge toward the center, a stable vortex is produced. This vortexing flow of the purge air acts as a shield to prevent the entry of the sample into the purge chambers 106 and 108. If the purge air inlets were centered, a random turbulent flow of the purge air would occur in the purge chambers. With such a flow, a portion of the aerosol sample could enter the purge chambers from the scattering chamber and particles thereof deposit on the lenses.

The flow rate of the purge air is controlled by an orifice 118 located in the manifold 114 and is a small fraction of the flow rate of the aerosol sample stream. For example, when the flow rate of the serosol sample is approximately 1 cubic foot per minute, the total flow rate of purge air can be approximately 0.1 cubic feet per minute. The flow system for the areosol sample and the purge air preferably is otherwise arranged in the manner described in U.S. Pat. No. 3,787,122 which issued Jan. 22, 1974 and is incorporated herein by reference.

The photometer 10 can be adapted for analyzing a liquid sample by simply replacing the inlet nozzle 42 and the outlet conduit 44 with a cylindrical tube made from a transparent material which will not scatter light, such as glass. This tube is located in the housing so as to extend through the focal region 36 substantially perpendicular to the axis 20. Since the sample being analyzed is isolated from the lenses there is no need for a purge system.

One of the primary functions of the apertured discs 30, 38, 52 and 59 is the elimination of cylindrical optics, i.e., rays which cross the axis 20, strike the interior wall of the housing 12 at shallow angles and are then reflected back to the axis 20. Conventional light-absorbing coatings are much less effective at shallow, specular angles (equal incident and reflected angles). If the bore of the housing 12 is made several inches larger than the lenses 26 and 50, cylindrical optics are negligible and the discs 30 and 59 could be eliminated. When the photometer is being used for analyzing liquid samples and there is no need to provide for a purge system, the discs 38 and 52 also could be eliminated.

While the preferred embodiments of the invention have been illustrated and described in detail, it will be apparent to those skilled in the art that various alterations and modifications can be made thereto without departing from the spirit and scope of the invention.

I claim:

1. A forward light scattering photometer comprising an elongate housing;

a light source for providing a beam of light along an axial path through said housing;

first and second axially spaced, spherical-surfaced, bi-convex lenses located inside said housing and disposed coaxially with said axial path, said lenses providing axial focusing of an image of said lamp on said axial path with radial aberrations and substantially no circumferential aberrations;

a first light trap located in said housing adjacent the upstream side of said first lens, said first light trap including a light-absorbing area and a light-transmitting area, the border between said areas extending radially in a straight line relative to said axial path so as to form an image with sharp radial edges at the focal region between said lenses;

means for introducing a fluid sample containing particles through said focal region;

a second light trap located inside said housing adjacent the upstream side of said second lens, said second light trap having light-absorbing and light-transmitting areas which are complementary to those of said first light trap whereby the portion of the light beam passing through said focal region and not scattered by the sample particles is absorbed on the light-absorbing area of said second light trap and the portion of the light beam passing through said focal region and scattered forwardly by the sample particles passes through the light-transmitting area of second light trap; and light detecting means located downstream of said second lens for detecting the forwardly scattered light passing through said second lens and for producing a signal indicative of the number of particles in the sample.

2. A photometer according to claim 1 wherein said housing has a generally cylindrical bore and said photometer further includes first and second light-absorbing means located inside said housing between said focal region and said first lens and between said focal region and said second lens, respectively, each having an aperture disposed coaxially with said axial path through which said light beam passes, said first and second light-absorbing means cooperating with each other and with said housing bore to define a light scattering chamber and cooperating with respective of said first and second lenses and said housing bore to define a purge chamber associated with each of said lens; and means for introducing a stream of purge air into each of said purge chambers in a direction generally tangential to said housing bore so that said purge air flows through each of said purge chambers in a generally spiral pattern and exits therefrom into said scattering chamber through the respective of said light-absorbing means apertures.

3. A photometer according to claim 1 including first and second light-absorbing means located inside said housing between said focal region and said first lens and between said focal region and said second lens, respectively, each having an aperture disposed coaxially with said axial path through which said light beam passes, said first and second light-absorbing means cooperating with each other and with said housing bore to define a light scattering chamber.

4. A photometer according to claim 3 including
   a third light-absorbing means located in said housing between said light source and said first light trap and having an aperture disposed coaxially with said axial path through which said light beam passes; and
   a fourth light-absorbing means located inside said housing between said second trap and said light detecting means and having an aperture disposed coaxially with said axial path through which said light beam passes.

5. A photometer according to claim 4 wherein the aperture of said fourth light-absorbing means has a light-transmitting area which is substantially the same shape as and is substantially coaxial with the light-transmitting area of said second light trap.

6. A photometer according to claim 5 including
   a plate means located between said light source and said third light-absorbing means and having an aperture through which the light beam from said light source passes to said first lens, said plate means aperture having a light-transmitting area which is substantially the same shape as and is substantially coaxial with the light-transmitting area of said first light trap.

7. A photometer according to claim 6 including
   a third light trap located adjacent the downstream side of said first lens and having light-absorbing and light-transmitting areas which are substantially the same size as and are substantially coaxial with those of said first light trap; and
   a fourth light trap located adjacent the downstream side of said second lens and having light-absorbing and light-transmitting areas which are substantially the same size as and are substantially coaxial with those of said second light trap.

8. A photometer according to claim 1 wherein the light-absorbing areas of said first and second light traps are semicircular, are circumferentially aligned and mask at least one half of respective of said first and second lenses.

9. A photometer according to claim 1 wherein
   the light-absorbing and light-transmitting areas of said first and second light traps are radially extending sectors of a circle.

10. A photometer according to claim 4 wherein
    the light-absorbing areas of said first and second light traps are semicircular, are circumferentially aligned, and mask at least one half of respective of said first and second lenses; and
    the aperture of said fourth light-absorbing means is semicircular and is circumferentially aligned with the light-absorbing areas of said first and second light traps.

11. A photometer according to claim 10 including
    a plate means located between said light source and said first lens and having an aperture through which the light beam from said light source passes to said first lens, said plate means aperture having a semicircular opening which is circumferentially alinged with the light-transmitting areas of said first and second light traps.

* * * * *